(12) United States Patent
Eisenhardt et al.

(10) Patent No.: US 8,628,721 B2
(45) Date of Patent: Jan. 14, 2014

(54) SYSTEM FOR MEASURING AN ANALYTE CONCENTRATION OF A BODY FLUID SAMPLE

(75) Inventors: Christoph Eisenhardt, Mannheim (DE); Heino Eikmeier, Lorsch (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 700 days.

(21) Appl. No.: 12/638,347

(22) Filed: Dec. 15, 2009

(65) Prior Publication Data

US 2010/0119414 A1 May 13, 2010

Related U.S. Application Data

(63) Continuation of application No. PCT/EP2008/004293, filed on May 30, 2008.

(30) Foreign Application Priority Data

Jun. 15, 2007 (EP) ..................... 07011740

(51) Int. Cl.
*G01N 33/48* (2006.01)

(52) U.S. Cl.
USPC ....... 422/68.1; 422/430; 422/403; 422/82.05; 422/82.09; 702/25; 702/86; 702/87; 702/88; 356/39

(58) Field of Classification Search
USPC ............... 422/55, 56, 57, 58, 61, 68.1, 82.05, 422/82.09, 99, 119, 430, 403; 436/8, 12, 436/13, 14, 15, 16, 65, 66, 69, 70, 71, 164, 436/500, 501, 506, 510, 512, 513, 514, 517, 436/518, 536; 356/39; 702/22, 25, 86, 87, 702/88

See application file for complete search history.

(56) References Cited

U.S. PATENT DOCUMENTS

| | | | | |
|---|---|---|---|---|
| 3,907,503 A | * | 9/1975 | Betts et al. | 422/67 |
| 5,077,476 A | * | 12/1991 | Rosenthal | 250/339.04 |
| 5,281,395 A | * | 1/1994 | Markart et al. | 422/82.05 |
| 5,366,609 A | | 11/1994 | White et al. | |
| 5,597,532 A | | 1/1997 | Connolly | |
| 5,899,855 A | * | 5/1999 | Brown | 600/301 |
| 6,392,894 B1 | * | 5/2002 | Buechler et al. | 361/752 |

(Continued)

FOREIGN PATENT DOCUMENTS

| | | |
|---|---|---|
| DE | 10360786 A1 | 7/2005 |
| DE | 102004062255 B3 | 2/2006 |

(Continued)

*Primary Examiner* — Lyle Alexander
(74) *Attorney, Agent, or Firm* — Krieg DeVault LLP

(57) ABSTRACT

A system is provided for measuring an analyte concentration in a body fluid sample, comprising at least one cartridge that contains consumables for multiple measurements, a data carrier affixed to the cartridge that contains calibration information for the consumables, a hand-held device including a reading facility for receiving a cartridge of this type and for reading its data carrier, a measuring facility for measuring the result of a detection reaction, and a processor for controlling the measuring facility and for analysis of a measuring signal. At least one replaceable data storage unit is further provided in which supplementary data is stored. The data storage unit functions in combination with calibration information from the data carrier and is used by the processor to determine whether the consumables of the inserted cartridge renders a reliable measurement of analyte concentration.

17 Claims, 2 Drawing Sheets

(56) References Cited

U.S. PATENT DOCUMENTS

| | | | |
|---|---|---|---|
| 6,602,469 B1 * | 8/2003 | Maus et al. | 422/68.1 |
| 6,623,698 B2 * | 9/2003 | Kuo | 422/68.1 |
| 7,267,799 B1 * | 9/2007 | Borich et al. | 422/82.05 |
| 2003/0148530 A1 | 8/2003 | Lauks | |
| 2004/0260204 A1 * | 12/2004 | Boecker et al. | 600/584 |
| 2005/0187444 A1 | 8/2005 | Hubner et al. | |
| 2005/0201897 A1 | 9/2005 | Zimmer et al. | |
| 2007/0077175 A1 | 4/2007 | Harttig | |
| 2007/0081920 A1 * | 4/2007 | Murphy et al. | 422/58 |
| 2007/0084934 A1 | 4/2007 | Seppa | |
| 2007/0237678 A1 * | 10/2007 | Roesicke et al. | 422/82.01 |
| 2007/0255503 A1 | 11/2007 | Dodson | |
| 2008/0145277 A1 * | 6/2008 | Wohland | 422/82.01 |

FOREIGN PATENT DOCUMENTS

| | | |
|---|---|---|
| DE | 102004048864 A1 | 4/2006 |
| EP | 1424040 A1 | 6/2004 |
| EP | 1574855 A1 | 9/2005 |
| JP | 8-502590 | 3/1996 |
| JP | 2006-511818 | 4/2006 |
| JP | 2007-101542 | 4/2007 |
| JP | 2007-108174 | 4/2007 |
| RU | 2 263 354 C1 | 10/2005 |
| WO | WO 94/29703 | 12/1994 |
| WO | 96/13707 A2 | 5/1996 |
| WO | 02/100261 A2 | 12/2002 |
| WO | WO 2004/077052 | 9/2004 |
| WO | WO 2005/008574 A1 | 1/2005 |
| WO | 2006/023721 A1 | 3/2006 |

* cited by examiner

SYSTEM FOR MEASURING AN ANALYTE CONCENTRATION OF A BODY FLUID SAMPLE

CLAIM OF PRIORITY

The present application is a continuation application based on and claiming priority to PCT Application No. PCT/EP2008/004293, filed May 30, 2008, which claims the priority benefit of European Patent Application No. 07011740.3, filed Jun. 15, 2007, each of which are hereby incorporated by reference in their entireties.

TECHNICAL FIELD OF THE INVENTION

The present application relates to a system for measuring an analyte concentration in a body fluid sample, and more particularly to a system using cartridges holding multiple consumable test elements and having corresponding data carriers for conveying data about the disposable elements.

BACKGROUND

For testing of urine, blood, interstitial fluid or other body fluids, it is customary to use consumables containing detection reagents that effect a detection reaction when ex-posed to a body fluid sample. The detection reaction can, for example, lead to fluorescence or a color change that can be analyzed by photometry in order to determine an analyte concentration. Also known are detection reactions for electrochemical determination of an analyte concentration. In general, a detection reaction leads to a change in a parameter that can be measured physically, whereby the intensity of the change depends on the analyte concentration to be measured.

In a typical case, the detection sensitivity varies substantially between production batches of consumables containing detection reagents. For this reason, there is a need to have calibration data in order to be able to determine an analyte concentration with sufficient accuracy for medical applications when analyzing the result of a detection reaction from the extent of the change of a physical parameter, for example a change of color. Calibration data of this type is usually determined for each production batch using calibration liquids of known analyte concentration and a corresponding calibration information is stored on a data carrier that is distributed jointly with the consumable.

For this reason, hand-held devices of systems for measuring an analyte concentration of a body fluid sample usually contain, aside from a measuring facility for measuring the result of a detection result, a reading facility for reading calibration information from a data carrier. For example, one known system provides a bar code containing a calibration information, affixed to the outside of a drum cartridge containing the consumables. An exemplary disclosure is from EP 1 574 855. However, such systems are rather inflexible.

The production of hand-held devices of systems for measuring the analyte concentration in a body fluid sample is expensive since there is a need to have a highly-precise measuring facility and a processor as a control and analytical unit. As progress is made in the production of consumables with detection reagents, the software that was used to program the processor at the time the hand-held device was delivered may no longer meet the requirements of improved consumables, since, for example, different measuring parameters, for example different measuring times or even different measuring or analytical procedures may be needed. However, changing the programming of the microprocessor is not feasible in the hand-held device known, for example from EP 1 574 855 A1, such that progress made with regard to the measuring of the analyte concentration of a body fluid sample usually necessitates the purchase of a new hand-held device. Moreover, possibly existing software errors can be rectified only by a cost-intensive recall action.

It is therefore the object of the invention to further improve upon a system for measuring an analyte concentration of a body fluid sample of the type specified above. In particular, it is the object of the invention to devise a way allowing even medical laymen to carry out a reliable measurement of an analyte concentration of a body fluid sample at low cost.

SUMMARY

This object and others that will be appreciated by a person of ordinary skill in the art have been achieved according to the embodiments of the present invention disclosed herein.

In a system according to the invention, the software for programming the processor can be adapted to changed requirements using supplementary data that is stored in a separate data storage unit. The supplementary data cooperates in the analysis of a measurement signal with calibration information stored on the data carrier of the magazine inserted in the de-vice. Hence, according to embodiments of the invention, the supplementary data contain data that differs from the calibration information and assists in providing for a correct determination of an analyte concentration.

When consumables are updated or upgraded, no correct analyte concentration value can be determined by means of the calibration information alone because corresponding supplementary data for the processor is required as well. The supplementary data can enable a correct calculation of an analyte concentration from a measurement signal and/or specify the measurement process itself, i.e. the correct creation of a measurement. The supplementary data can, for example, comprise altered measuring or analytical parameters required by an update or upgrade of the consumables. A first set of supplementary data can be stored in a memory connected to a processor of the device upon manufacturing. When needed, altered supplementary data can be read from a data storage unit, which can be separate from the magazine.

The different functions of a data carrier in which the calibration information is stored and the data storage unit in which supplementary data is stored are therefore that in the data carrier production hatch specific data is stored, i.e. data that typically change with each production batch, whereas the supplementary data stored in the data storage unit can be used for consumables of several production batches. The most important batch specific data is calibration information. Additionally, further supplementary data, like manufacturing or expiration dates, may be stored in the data carrier.

Furthermore, the software of a system according to the invention can be adapted to altered requirements by means of data stored in the data storage unit. So the supplementary data can contain in addition to changed measurement or analysis parameters also, e.g., software updates, especially for a user interface respectively menu or operating functions, for a motor control, for evaluation of measured data or an interface to external devices. Although supplementary data of this type can be quite voluminous, it is needed rather infrequently such that data memories containing supplementary data are also needed infrequently only. For this reason, the cost of data memories containing supplementary data is negligible as compared to the cost of cartridges containing consumables of which a typical user needs much larger numbers.

In order to be able to change the programming of a microprocessor according to need, the present invention did not select a way in which, in addition to the calibration information, supplementary data that could be used to change the programming of the microprocessor in the hand-held device is also stored on the data carrier affixed to the cartridge. If this data was stored on the data carrier affixed to the cartridge, it would be possible to safely ensure that the current data including calibration information needed for measurements using the consumables of an inserted cartridge is available to the processor of the hand-held device at all times. Moreover, a solution of this type would be user-friendly, since a user would not need to perform any additional actions in order to transmit the supplementary data to the hand-held device.

However, as part of the present invention, it was recognized that these advantages can be attained with embodiments of a system according to the invention in a significantly less expensive fashion. Since supplementary data such as, for example, software updates is needed only infrequently, the storage of supplementary data on the data carrier of a cartridge would necessitate having a powerful and therefore relatively expensive memory for each cartridge which, in turn, would lead to noticeably higher costs of the cartridges which are produced in large numbers. These higher cartridge costs can be avoided according to the embodiments of the invention by storing on the data carrier that is affixed to the cartridge only a relatively small set of data, in particular the calibration information that is required individually by each cartridge, whereas a larger, more rarely changing set of data including supplementary data is stored in a separate data storage unit that is delivered and changed in the hand-held device only if the need arises, for example when supplementary data are required because of modified consumables.

In the case of a hand-held device, the invention requires at most minimal additional costs that are related to an interface for transmitting supplementary data that is stored on the data storage unit to the hand-held device. This contrasts favorably to the substantial cost savings related to the data carrier that is affixed to the cartridge, which data carrier can, for example, be provided in a cost-efficient fashion in the form of a barcode carrier, such as is disclosed in EP 1 574 855 A 1.

Despite the division of calibration information and supplementary data to a data carrier on the cartridge and a replaceable data storage unit for the hand-held device, respectively, it can be excluded in a system according to the invention that consumables are used with supplementary data that is not suitable for use with these consumables, which could lead to erroneous measuring results and an ensuing health risk for a user, unless it was excluded. This is provided by the fact that a consumables identification is stored jointly with the calibration information on the data carrier and allows the processor to check whether the consumables of an inserted cartridge can be used in combination with the supplementary data that is available to the processor to carry out a reliable measurement of an analyte concentration in a body fluid sample. If the microprocessor determines that this is not the case, for example because a required update has not yet been carried out, a signal is generated to alert the user to this fact.

The invention is to be explained in more detail by the following figures and examples.

BRIEF DESCRIPTION OF THE DRAWINGS

The following detailed description of the embodiments of the present invention can be best understood when read in conjunction with the following drawings, where like structure is indicated with like reference numerals and in which.

In order that the present invention may be more readily understood, reference is made to the following detailed descriptions and examples, which are intended to illustrate the present invention, but not limit the scope thereof.

DETAILED DESCRIPTION OF EMBODIMENTS OF THE PRESENT INVENTION

The following descriptions of the embodiments are merely exemplary in nature and are in no way intended to limit the present invention or its application or uses.

Figure 1:
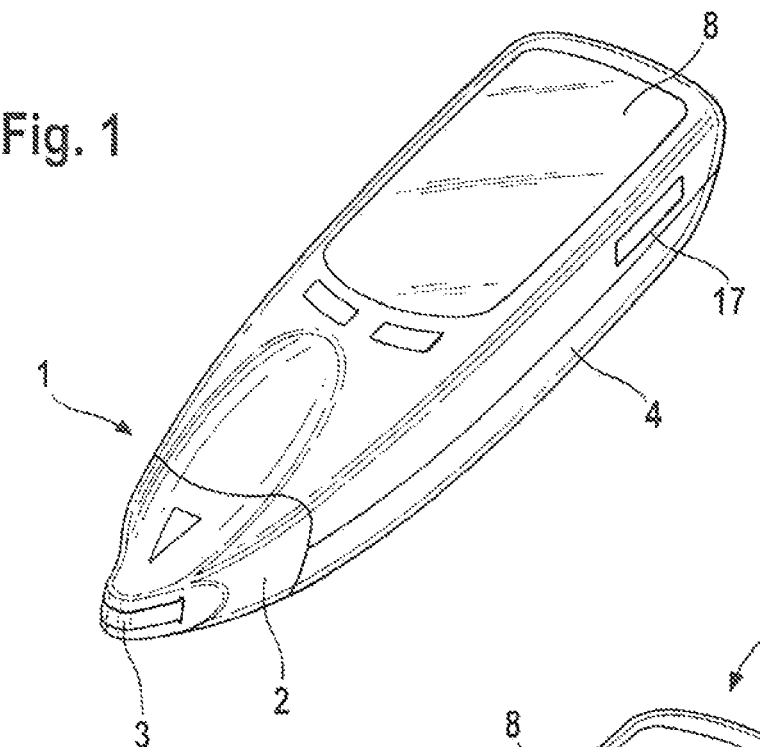
FIG. 1 shows a schematic view of an exemplary embodiment of a system according to the invention for measuring an analyte concentration of a body fluid sample.

FIG. 1 shows a system 1 for measuring an analyte concentration in a body fluid sample, for example for measuring the glucose concentration of blood and/or interstitial fluid. Systems of this type are needed, for example, by diabetics, who need to measure their blood sugar level multiple times daily. The system 1 shown comprises at least three separate system components, namely a cartridge 2 including consumables 3 shown in FIG. 2, a hand-held device 4 shown in FIG. 3 which, according to its intended purpose, receives the cartridge 2, and a replaceable data storage unit 5 including supplementary data for the hand-held device 4.

These system components 2, 4, 5 are illustrated in more detail in the following with reference being made to the corresponding figures.

Figure 2:
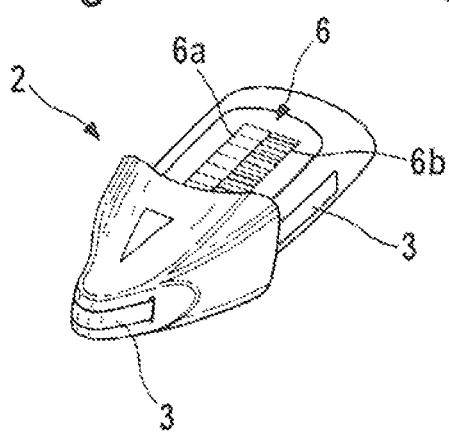
FIG. 2 shows a replaceable cartridge including consumables.

FIG. 2 shows an exemplary embodiment of a cartridge 2 that contains consumables 3 for multiple measurements. In the exemplary embodiment shown, the consumables 3 are a tape that carries detection reagents that effect a detection reaction when they are exposed to a body fluid sample. The detection reaction leads to a change of color of the tape section wetted by the body fluid sample. This change of color can be analyzed by photometry in order to determine the analyte concentration of the applied body fluid sample, i.e. being the glucose concentration in the exemplary embodiment shown. In the exemplary embodiment shown, the strip 3 is gaplessly provided with detection reagents, e.g. covered by or impregnated with them. However, it is also feasible to apply the detection reagents to the strip 3 in individual test fields only. In particular, lancets could be arranged on the strip between test fields of this type in order to generate a cartridge for a hand-held device that can be used to generate a puncture wound for obtaining a body fluid sample and subsequent testing of the body fluid sample thus obtained.

The tape 3 in the cartridge 2 is wound onto a storage reel (not shown), but can just as well, for example, be folded in a zigzagging fashion to form a stack. The cartridge contains a conveyor reel that can be driven (not shown) onto which the spent section of the tape 3 is wound. By rotating the conveyor reel, a fresh, i.e. unused, tape section can be moved to a sample reception position, in which it can be wetted by a body fluid sample. By rotating the conveyor reel further, a tape section to which a body fluid sample has been applied can be conveyed to a measuring position and a fresh tape section can be moved to the sample reception position for another measurement.

To the cartridge 2 is affixed a data carrier 6 that is manufactured by a printing procedure in the exemplary embodiment shown and carries the data, for example, in the form of bar code. It is also feasible, for example, to provide the data carrier 6 in the form of an OTP (one-time programmable) or magnetic memory. It is also feasible, for example, to provide the data carrier 6 in the form of a printed electronic memory that is contacted by the reading facility 10 of the hand-held device 4 for the purpose of read-out. For example, the data carrier 6 may be provided as a resistor array, wherein the data stored therein are encoded by different resistance values. It is also possible that the data carrier 6 has differently colored areas which encode data.

The data carrier 6 contains a calibration information for the consumables 3 that are contained in the cartridge 2. The bar code is read upon insertion of the cartridge 2 in a cartridge reception compartment 7 of a hand-held device 4 that is part of the system 1. Since the speed of insertion varies between users, the data carrier 6 shown has a feed track 6a with equidistant feed marks and an information track 6b that contains the calibration information. Other technical solutions for reading a bar code are also possible. In particular, bar code readers can be used advantageously which do not require a relative movement between the hand-held device 4 and the data carrier, i.e. which can read a data carrier 6 that is at rest with respect to the hand-held device 4. Such bar code readers can, e.g., have a CCD line so that the whole bar code can be read without any relative movement.

In the exemplary embodiment shown, the cartridge 2 including the consumables 3 is provided in the form of a tape cassette. However, it is also feasible to provide the cartridge in the form of a drum cartridge such as is known, for example, from EP 1 574 855 A1.

Figure 3:
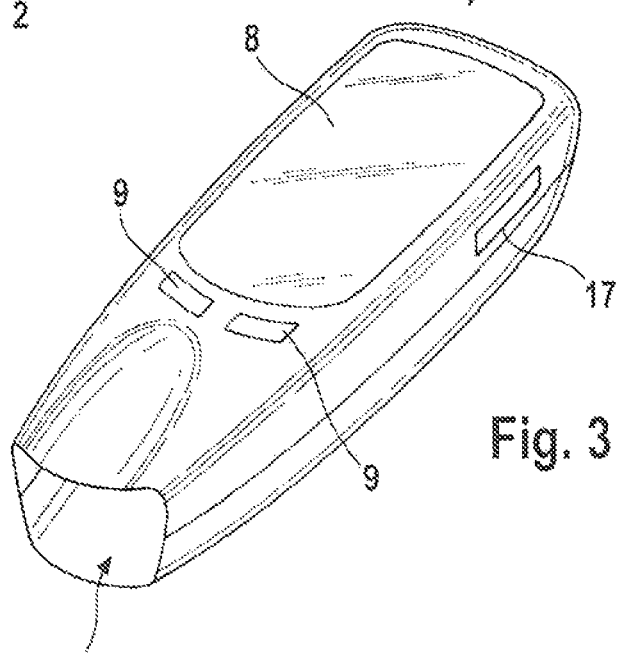
FIG. 3 shows a hand-held device, in which the cartridge shown in FIG. 2 can be inserted.

The cartridge 2 shown in FIG. 2 can be inserted in a cartridge reception compartment 7 of the hand-held device 4 shown in FIG. 3. The hand-held device 4 shown has approximately the size of a cellular telephone and is therefore easy to carry along in a jacket pocket by a user. The hand-held device 4 can be operated independent of mains supply, for example by means of batteries. Measuring results can be displayed by a display facility 8, for example by a liquid crystal display. For its operation, the hand-held device 4 further comprises operating elements 9 which are provided in the form of keys in the exemplary embodiment shown.

Figure 5:
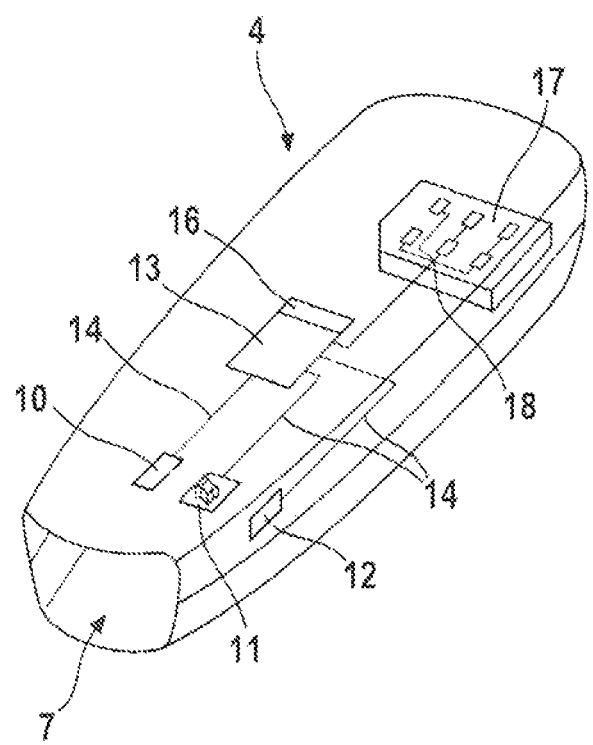
FIG. 5 shows a schematic view of the components of the hand-held device shown in FIG. 3.

The internal layout of the hand-held device 4 shown in FIG. 3 is shown schematically in FIG. 5 to which reference shall also be made in the following. The hand-held device 4 has a cartridge reception compartment 7 with a reading facility 10 in order to receive a cartridge 2, that is shown in FIG. 2 and read a data carrier 6 that is affixed to said cartridge 2. By means of a transport facility 11, consumables 3 of a cartridge 2 that is inserted in the cartridge reception compartment 7 can be moved for reception of a sample and measurement of the analyte concentration in a received body fluid sample. The transport facility 11 for transporting the tape 3 can, for example, be provided like in an audio tape recorder. To prevent slippage, the transport facility could also comprise an index wheel with cogs that engage consecutive perforations of the tape 3. In the exemplary embodiment shown, the transport facility 11 ac-cording to FIG. 5 comprises a shall having a head that deviates from circular shape, for example, a star-shaped head, that engages a matching recess of the drivable conveyor reel of the cartridge 2 shown in FIG. 2. After reception of a sample, the tape 3 can be moved further by the transport facility 11 such that a tape section wetted by the sample is moved to a measuring position, in which the result of a detection reaction, for example the degree of a change of color that is effected by an analyte that is to be detected, is measured by a measuring facility 12 of the hand-held device 4.

The transport facility 11, the measuring facility 12, and the reading facility 10 are controlled by a processor 13 to which they are connected by means of data lines 14. The processor 13 analyzes measuring signals measured by the measuring facility 12 in order to determine a concentration value to be displayed by means of the display facility 8. A memory 16, in which software for the processor 13 is stored, is connected to the processor 13. The processor 13 and its memory 16 can be components of a microcontroller or microcomputer.

Figure 4:
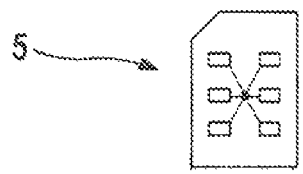
FIG. 4 shows a replaceable data storage unit for the hand-held device shown in FIG. 3.

Another separate system component that is part of the system shown in FIG. 1 is a replaceable data storage unit 5 that is shown in FIG. 4 and can be inserted in a reception compartment 17 of the hand-held device 4 shown in FIG. 3. The reception compartment 17 is accessible through a slit in the housing of the hand-held de-vice 4.

Data stored in the data storage unit 5 can be transmitted to the hand-held device by means of an interface of the hand-held device 4. In the exemplary embodiment shown, the interface contains a reading facility 18 for reading a data storage unit 5 that is inserted in the reception compartment 17.

The replaceable data storage unit 5 can, for example, be an EEPROM, in particular a flash-EEPROM, a Smartcard or any other memory chip. However, in principle, it is also feasible to provide the replaceable data storage unit in the form of a RFID memory and transmit data to the hand-held device 4 by means of a wireless interface such that a reception compartment for the data storage unit 5 is dispensable. It is also possible that the manufacturer fixes the data storage unit 5, when needed, on the magazine so that no separate reception compartment is necessary.

The data storage unit 5 stores supplementary data that functions in concert with calibration information, which is stored on the data carrier 6 of a cartridge 2 that is inserted in the device 4, and the software that is stored in the memory 16 of the hand-held device 4 during the analysis of a measuring signal. The supplementary data can, for example, set measuring or illumination times for controlling the measuring facility 12. The data carrier 5 allows the system provider to change or replace measuring or analytical algorithms according to need and in this way adapt the hand-held device 4 to changed requirements that may result from improved consumables 3. In addition to data, which together with the calibration information is strictly necessary for a correct determination of an analyte concentration, the supplementary data may also contain conventional software updates, for example to change a user interface.

Supplementary data stored in the replaceable data storage unit 5 can be copied into the memory 16 of the hand-held device 4 such that the data storage unit 5 can be taken from the reception compartment 17 after read-out. After read-out, the supplementary data can be deleted from the data storage unit 5 in order to render misuse more difficult. However, it is also feasible to dispense with storing the supplementary data in the memory 16 of the hand-held device such that the hand-held device 4 can be operated only while the data storage unit 5 is inserted therein.

The data carrier 6 of the cartridge 2 shown in FIG. 2 stores a consumables identification that is used by the processor 13 after insertion of the cartridge 2 to determine whether the consumables 3 of the inserted cartridge 2 combined with the supplementary data that is available to the processor 13 renders a reliable measurement of the analyte concentration in a body fluid sample feasible. If this is the case, a measurement of the analyte concentration in a body fluid sample can be carried out. If this is not the case, the processor 13 generates a signal in order to indicate to a user that the available supplementary data and the consumables 3 of the inserted cartridge 2 do not allow a valid measurement of the analyte concentration in a body fluid sample to be carried out. The signal generated by the processor for this purpose can effect any action of the hand-held device 4 that allows a user to recognize that the available supplementary data and the consumables 3 of the inserted cartridge 2 do not allow a valid measurement of the analyte concentration in a body fluid sample to be carried out. The signal of the processor 13 can, for example, induce the display facility 8 to display a corresponding message and/or cause an acoustic signaling facility to generate an acoustic signal.

By this means, it is feasible to reliably achieve that consumables 3 of the system 1 are used exclusively in combination with supplementary data intended by its manufacturer for this purpose, in particular suitable and current algorithms. Particularly in case that the supplementary data effects a modification of the algorithm that is stored in the memory 16 of the hand-held device 4, the performance and analysis of a measurement using consumables 3 with different prerequisite supplementary data can lead to incorrect measuring results. A corresponding signal can be displayed to the user, for example, by means of the display facility 8. Also suitable for this purpose are acoustic signals, for example beeping sounds. It is particularly useful to transmit the warning signal indicating that no valid measurement can be carried out with the available system components 3, 4, 5, both acoustically and optically.

Further hatch-specific data characterizing the consumables of a production batch can be stored on the data carrier 6 affixed to the cartridge 2. Consumables 3 including detection reagents are typically produced in hatches, whereby the individual production batches differ in terms of their sensitivity due to inevitable variations of the production process such that calibration information is required for the analysis of measurements carried out using the consumables 3. The calibration information can explicitly specify the sensitivity of the consumables 3 and can, for example, explicitly specify for one or more supporting points, from which an analytical curve can be generated, the intensity of the change of parameter that is associated with the detection reaction, for example the degree of the change of color to be analyzed by photometry, for one or more analyte concentrations. It is also feasible that the memory 16 of the hand-held device stores a library of analytical curves and the calibration information simply specifies the number of the analytical curve to be used.

Aside from the calibration information, for example the production date and/or expiry date is further batch-specific information. Moreover, by storing information on the data carrier 6 from which information the processor 13 can determine an expiry date for the consumables 3 that are contained in the cartridge 2, it can be excluded that erroneous measuring results are obtained because of the use of obsolete and therefore unreliable consumables.

For this reason, after insertion of a cartridge 2 in the cartridge reception compartment 7 of the hand-held device 4, the processor 13 of the exemplary embodiment shown checks not only whether or not the calibration information matches the available supplementary data, but also whether or not an expiry date of the consumables of the inserted cartridge has already expired. If this is the case, the user will be alerted to this fact.

Whereas the data carrier 6 of the exemplary embodiment contains all batch-specific data needed for a measurement, the data storage unit 5 can be configured so that it exclusively stores data that can be used for measurements using consumables 3 from multiple and if applicable, different cartridges 2. Accordingly, the data storage unit 5 of such embodiments contains non-hatch-specific data exclusively that can be used with multiple cartridges without a need for changes. Only when a need for changed supplementary data be-comes evident, for example for adaptation to improved consumables 3 or for rectification of recognized weaknesses of the software, newly produced cartridges 2 are provided with a new identification such that the hand-held device 4 alerts the user to the existence of a need for new supplementary data provided it does not yet know the identification of a new cartridge.

Typically, less than 200 bit are stored on the data carrier 6, since this is generally sufficient for an identification, a calibration information, and other batch-specific in-formation. In the exemplary embodiment shown, the data storage unit 5 has a larger memory capacity than the data carrier 6. In general, in excess of 500 bit, in particular in excess of 1 kbit, are stored in the data storage unit 5. In case of extensive software updates, significantly larger data quantities can be stored in the data storage unit 5.

The features disclosed in the above description, the claims and the drawings may be important both individually and in any combination with one another for implementing the invention in its various embodiments.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

What is claimed is:

1. A system for measuring an analyte concentration in a body fluid sample, comprising consumables having a plurality of test fields with detection reagents that effect a detection reaction when exposed to the body fluid sample, at least one cartridge that contains consumables of this type for multiple measurements, a data carrier which is affixed to the cartridge and contains calibration information for the consumables contained in the cartridge, said calibration information specifying sensitivity of a test field, and a hand-held device that comprises a display facility and a cartridge reception compartment including a reading facility for receiving a cartridge of this type and for reading its data carrier, a measuring facility for measuring the result of a detection reaction, a transport facility for moving consumables of the cartridge that is inserted in the cartridge reception compartment, for reception of a sample and measurement of the analyte concentration in the received body fluid sample, a processor that is connected to the measuring facility and the reading facility for controlling the measuring facility, said processor being adapted for determining a concentration value by analyzing the measuring signal, and a memory that is connected to the processor and contains software for the processor, the system further comprising at least one replaceable data storage unit in which supplementary data is stored that functions in combination with the calibration information that is stored on the data carrier of the cartridge that is inserted in the device during the analysis of a measuring signal, the hand-held device comprising an interface for transmission of supplementary data from the replaceable data storage unit to the device, and a consumables identification being stored on the data carrier and configured to be used by the processor after insertion of the cartridge to check whether the calibration information of the data carrier affixed to the inserted cartridge matches the available supplementary data and thereby to enable the system to determine whether the consumables of the inserted cartridge combined with the supplementary data that is available to the processor renders a reliable measurement of an analyte concentration in the body fluid sample feasible, or if determined no feasible then to generate a signal in order to indicate to a user that the available supplementary data and the consumables of the inserted cartridge do not allow a valid measurement of an analyte concentration in the body fluid sample to be carried out.

2. The system according to claim 1, wherein the supplementary data is configured to effect a modification of evaluation algorithms stored in the memory of the hand-held device.

3. The system according to claim 1, wherein the supplementary data is configured to effect a modification of the software that is stored in the memory of the hand-held device.

4. The system according to claim 1, wherein the data carrier further comprises batch-specific data characterizing the consumables of a production batch stored thereon.

5. The system according to claim 1, wherein the data storage unit exclusively stores data that can be used for measurements using consumables from multiple cartridges.

6. The system according to claim 1, wherein the hand-held device comprises a reception compartment for the data storage unit in which supplementary data is stored, and a reading facility containing the interface for read-out of the data storage unit that is inserted in the reception compartment.

7. The system according to claim 6, wherein the hand-held device comprises a housing having a slit through which the data storage unit can be inserted into the reception compartment.

8. The system according to claim 5, wherein the data storage unit is affixed to the cartridge.

9. The system according to claim 1, wherein less than 200 bit are stored on the data carrier.

10. The system according to claim wherein the data storage unit stores in excess of 500 bit, or data.

11. The system according to claim 1, wherein the data carrier comprises one of a bar code and a magnetic memory.

12. The system according to claim 11, wherein the hand-held device comprises a bar code reader which comprises a CCD line.

13. The system according to claim 1, wherein the data carrier comprises an arrangement of resistors, wherein the calibration information is encoded by different resistance values.

14. The system according to claim 1, wherein the data storage unit is an EEPROM.

15. The system according to claim 1, wherein the data carrier carries a code comprising a plurality of differently colored areas.

16. A cartridge with a data storage unit for a hand-held device for measuring an analyte concentration in a body fluid sample, the cartridge containing consumables having a plurality of test fields with detection reagents for multiple measurements, said detection reagents effecting a detection reaction when exposed to the body fluid sample, wherein a data carrier is affixed to the cartridge, said data carrier containing calibration information for the consumables contained in the cartridge, said calibration information specifying sensitivity of a test field, supplementary data being stored in the data storage unit, said supplementary data functioning during the analysis of a measuring signal in combination with the calibration information that is stored in the data carrier of the cartridge inserted in the device, and a consumables identification being stored on the data carrier, said consumables identification being configured to allow the hand-held device to check whether the calibration information of the data carrier affixed to the cartridge matches the supplementary data stored in the data storage unit in order to determine whether a valid measurement of an analyte concentration in the body fluid sample can be carried out with the consumables of the cartridge in combination with the available supplementary data.

17. The cartridge according to claim 16, wherein the data storage unit is affixed to the cartridge.

* * * * *